May 12, 1953 C. WHITE Plant Pat. 1,186
JUNIPER PLANT
Filed Nov. 23, 1951
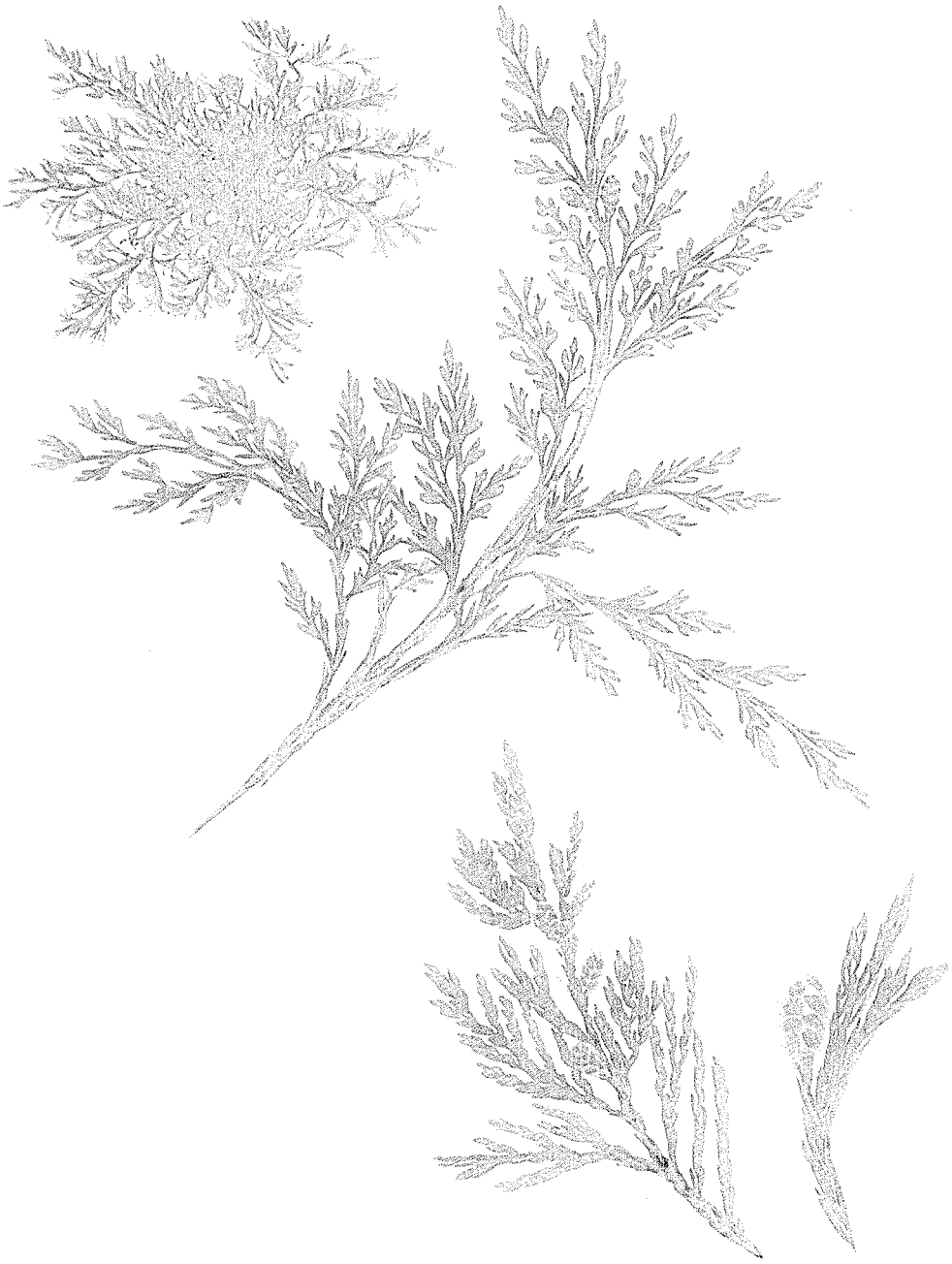
INVENTOR.
Carl White
BY Greek Wells
atty Patented May 12, 1953

Plant Pat. 1,186

UNITED STATES PATENT OFFICE 1,186

JUNIPER PLANT

Carl White, Walla Walla, Wash.

Application November 23, 1951, Serial No. 257,708

1 Claim. (Cl. 47—59)

My discovery relates to a new and distinct variety of prostrate evergreen plant of the species *Juniperus scopulorum* having certain desirable characteristics as an ornamental evergreen among which may be mentioned the following:

The coloring of all of the foliage is silver gray, very similar to that of the upright trees of the species *Juniperus scopulorum*, the new buds being gray and yellow striped as shown. There is very little difference in the coloring of old and new foliage.

The foliage is feathery and soft.

The habit of growth is low and spreading, the height and spread resembling that of the Andorra spreading juniper. In six years it has attained a height of approximately eight inches and a spread of about five feet.

The stems age to a light brown and show rather clearly when viewed from above the plant.

More specifically this new variety of evergreen plant is described as follows, color designations being as found in "Color Standards and Color Nomenclature by Ridgway—1912":

*General characteristics.*—Prostrate spreading relatively fast growing compact at center with shaggy tips.

*Branches.*—Irregular, interlaced.

*Colors.*—Old stems wood brown, Plate XL, hue 17''', tone *b* to *j*.

*Leaves.*—Compact, slightly, acuminate, outer surface convex.

*Color.*—Varying from body of winter green, Plate XVIII, to edges of pale glaucus green, Plate XXXIII, blending to give an overall greenish silver gray.

*Buds.*—Ovate, larger end remote from stem.

*Color.*—Striped transversely, base being winter green, Plate XVIII and the stripes being light greenish yellow, Plate V, to pale lemon yellow, Plate IV.

In the drawing I have attempted to illustrate a prostrate juniper characteristic of the present improved variety, and therein:

The upper left hand view illustrates the general habit of growth;

The central view shows a branch with old and new growth on a slightly reduced scale;

The lower right hand views illustrate small branches, the bud on the right hand one of these views illustrating the characteristic bud pattern.

The original plant was obtained by planting seed from an upright tree of the species *Juniperus scopulorum*, commonly called Colorado silver juniper. The tree was not of a patented variety. I planted the seed and grew the original plant at my nursery at Walla Walla, Washington. This plant showed its peculiar spreading characteristics as soon as it began to branch which was in the spring of 1945. In 1946 I first began to reproduce the plant by cuttings and I have been taking cuttings and starting new plants from the original plant and other plants started from the cuttings of the original plant. All of the new plants I have started show the same characteristic coloring of the foliage and branches, the freedom from sharp needles and spreading growth of the original plant.

I have reproduced this new spreading juniper only by cuttings and up to the present time I retain possession of the original plant and of all the plants grown from cuttings, at my nursery at Walla Walla, Washington. This variety of plant has not been characterized or described in print up to the present date.

I claim:

The new and distinct variety of juniper plant as described and illustrated, characterized by its prostrate spreading shape, the foliage being feathery and being predominantly greenish silver gray in color, the aged branches being substantially wood brown and the buds being green and yellow striped.

CARL WHITE.

References Cited in the file of this patent

UNITED STATES PATENTS

| Number | Name | Date |
|---|---|---|
| Pl. Pt. 1,070 | Pinney | Jan. 29, 1952 |